United States Patent [19]

Bartlett

[11] Patent Number: 4,547,186
[45] Date of Patent: Oct. 15, 1985

[54] AUTOTRANSFUSION SYSTEM

[76] Inventor: Robert H. Bartlett, 3870 Waldenwood, Ann Arbor, Mich.

[21] Appl. No.: 472,763

[22] Filed: Mar. 7, 1983

[51] Int. Cl.[4] .......................... A61M 1/00; A61M 4/00
[52] U.S. Cl. .......................................... 604/4; 604/7; 128/DIG. 3; 128/DIG. 12
[58] Field of Search ................ 604/28, 29, 902, 269, 604/5–10, 51–53, 67; 210/321.2; 422/44; 128/DIG. 3, DIG. 12, DIG. 13

[56] References Cited

U.S. PATENT DOCUMENTS

| | | | |
|---|---|---|---|
| 3,625,212 | 12/1971 | Rosenberg | 128/214 R |
| 4,014,329 | 3/1977 | Welch et al. | 604/28 |
| 4,047,526 | 9/1977 | Reynolds | 128/214 R |

*Primary Examiner*—C. Fred Rosenbaum
*Assistant Examiner*—Mario Costantino
*Attorney, Agent, or Firm*—Lothrop & West

[57] ABSTRACT

A system for autotransfusion has an aspirating wand or tube coupled to a vacuum source through a reservoir for receiving aspirated blood. From that reservoir blood flows to a receiving bag in a relatively low position below the elevation of the patient. When there is sufficient blood supply in the bag, the bag is elevated from its lower position to a point higher than the patient. Blood then flows from the elevated bag by gravity through a conducting tube and a needle into the patient. When the bag is then substantially empty, it is again lowered to an elevation lower than the patient for repetition of the operation. If desired, an anticoagulant can be introduced into the aspirated blood.

13 Claims, 2 Drawing Figures

AUTOTRANSFUSION SYSTEM

BRIEF SUMMARY OF THE INVENTION

A bag holding blood for autotransfusion from and to a patient is disposed at an elevation lower than the patient while receiving blood from the patient. The bag is then disposed at an elevation higher than the patient and at that time discharges the blood to the patient. An anticoagulant may be incorporated with the transfusion blood.

DETAILED DESCRIPTION

Figures 1, 2:
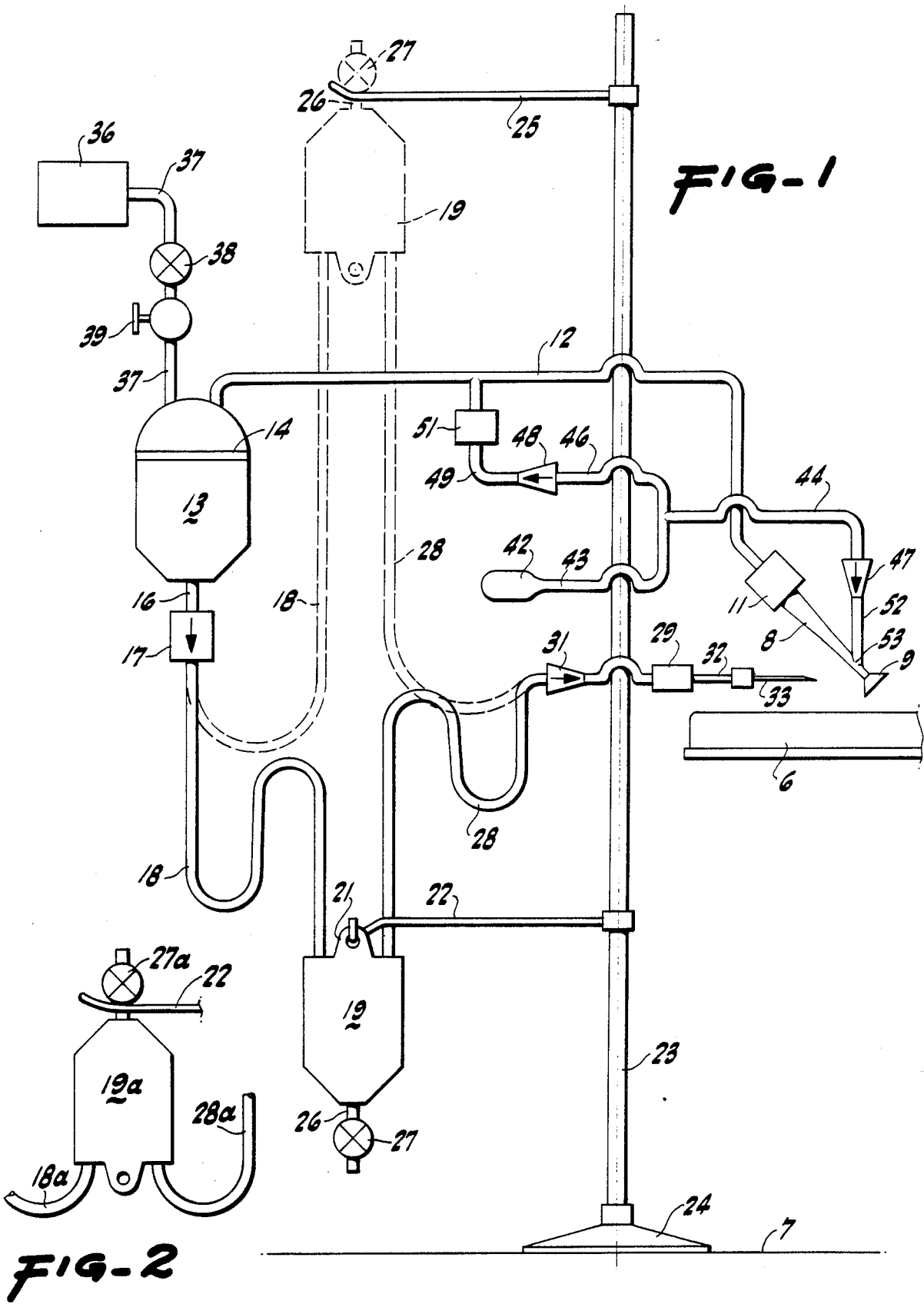
FIG. 1 is a diagram showing a typical embodiment of an autotransfusion system pursuant to the invention.
FIG. 2 is a detail, with portions broken away, showing a modified form of blood bag.

The transfusion system pursuant to the invention is especially adapted for use with a patient lying on a table 6 at a chosen elevation above a floor 7. The apparatus includes an induction conduit such as a wand 8 or tube for aspirating blood from the patient substantially at the elevation 6. The wand is operated under vacuum and has an entrance nozzle 9 and a handle 11 for convenient manipulation. The vacuum wand is connected through a flexible tube 12 to a reservoir 13 of any convenient configuration, preferably a generally closed vessel having a suitable defoamer and filter 14 therein.

From the reservoir 13 there is a flexible outlet tube 16 passing through a check valve 17 opening in the outflow or downward direction and closing in the opposite direction. The valve 17 is connected by a flexible conduit 18 to a blood bag 19. Conveniently, the blood bag 19 is of a flexible or expansible nature and is expandable and collapsible by differences in pressure between the inside and the outside thereof. The bag 19 can be removably suspended, in an upright position, by means of a perforated hanging tab 21 at one end, engageable with a lower hook 22 extending laterally from an upright stand 23 having a base 24 resting on the floor 7. With this arrangement, as shown in FIG. 1, the flexible conduit 18 enters into the portion of the bag 19 that is then uppermost.

The bag at the end opposite the hanging end or tab 21 has an end tube 26 provided with a manually operable valve 27. From the end of the bag receiving the tube 18 there is a flexible tube 28 leading to a conventional blood filter 29. There is a one-way check valve 31 interposed in the line 28 so that flow from the bag 19 to the filter 29 is easily possible, but reverse flow is precluded. From the filter 29 there is a discharge tube 32 leading to a needle 33 or the like for insertion into the patient to restore the blood.

In order that there may be appropriate blood flow into the receiver 13, there is afforded a vacuum source 36 of any suitable kind. This is connected by a pipe 37 through a manual shutoff valve 38 and a pressure regulator 39 to the upper portion of the reservoir 13. When the vacuum mechanism 36 is operating and the valve 38 is open and the regulator 39 is set, there is afforded within the reservoir and its connections a predetermined subatmospheric pressure adequate to lift blood from the entrance 9 of the wand 8 into the upper portion of the reservoir.

It is often desired to provide an anticoagulant for the just-aspirated blood in order to maintain its flowing capabilities. For that reason, there may be provided an anticoagulant such as a solution containing sodium citrate in a conveniently movable bag 42. This bag is readily adjusted or positioned vertically and is provided with a flexible tube 43 having a flexible branch 44 and a branch 46. The branch 44 has a check valve 47 in it allowing flow away from the citrate bag 42, whereas the branch 46 has a valve 48 in it also allowing flow away from the citrate bag. The valve 47 is joined at an appropriate angle by a duct 52 to an entry 53 to the wand 8 near the nozzle 9. The valve 48 is joined by a connector 49 to the tube 12 at a point remote from the wand. Preferably, there is a restriction 51 in the tube 49 immediately in advance of the tube 12 in order to throttle the rate of anticoagulant flow.

In the operation of this mechanism, the vacuum source 36 is started and the bag 19 is initially stationed on the lower hook 22. When the valve 38 is open, vacuum or subatmospheric pressure is furnished through the regulator 39 to the receiver or reservoir 13 and is also made effective through the line 12 at the inlet 9 of the wand 8. The wand 8 is positioned at the level of or above the table 6 appropriate for use for collecting blood from the patient. All anticoagulant fluid lines are completely primed with anticoagulant from the anticoagulant bag 42. This is accomplished by transiently covering the opening of the nozzle 9, or by raising the level of the anticoagulant bag 42 above the levels of the two sites of anticoagulant introduction (i.e., the site of entry from the restriction 51 into the tube 12 and the site of the entry 53), or by a combination of the two processes. The anticoagulant bag 42 is then positioned at a level such that anticoagulant flows by gravity to the wand 8. The bag 42 is then carefully lowered to a final position at which the gravity flow of anticoagulant to the wand just ceases. The user, by grasping the handle 11 of the wand, introduces the nozzle 9 into the pool of blood available from the patient on the table 6. Such blood is induced to flow into the system, anticoagulant is drawn in at its two sites of introduction for mixing with the blood, and the anticoagulated blood continues into the reservoir 13.

The blood in the reservoir 13 flows by gravity despite the operation of the vacuum mechanism and passes downwardly through the tube 16 and through the valve 17 as well as the flexible conduit 18 into the bag 19 in its lowermost position. There can be no blood flow from the patient through the tube 28 at any time because closure of the check valve 31 precludes this. The withdrawn blood enters the bag 19, gradually distending the walls of the bag until the bag is substantially full.

At that time, with the valve 27 remaining closed, the bag 19 is removed from the lowermost hook 22 and is lifted and held in the position shown in FIG. 1 with the valve 27 in an uppermost position. The previously closed valve 27 is then opened. Any air trapped in the bag is allowed to vent from the bag. Also, the flexible bag can be squeezed to assist in the discharge of any air. Upon completion of this de-airing process, the valve 27 is closed. The bag 19, when placed so that it occupies a high or upper position hanging from an upper hook 25 supported by the stand 23, is at an elevation substantially above that of the patient on the table 6. The tubes 18 and 28 flex during the operation. Then, the bag 19 by gravity releases its contained blood through the flexible tube 28. Flow is through the now-open check valve 31 and filter 29 into the injecting device 33, and his blood is thus returned to the patient. During this outflow, the walls of the bag 19 tend to collapse until the bag is substantially empty.

While there is outflow from the raised bag 19, blood may still be aspirated from the patient through the entry nozzle 9 since the reservoir 13 is effective to receive such blood under the influence of the vacuum source 36, the valve 17 being closed by vacuum and the pressure of the column of blood in the raised tube 18.

When the bag 19 is empty, the bag is removed from the upper hook 25 and is again restored to a dependent position on the lower hook 22. In this restored position of the bag, blood from the reservoir 13 can resume its discharge therefrom through the valve 17 and the flexible conduit 18 and can refill and distend the bag 19 again. This cyclic, low and high operation of the bag 19 can be repeated from time to time to provide a transfusion as comprehensive as desired.

The cyclic, low and high operation of the bag 19 for delivering blood from the reservoir 13 back to the patient may also be used with blood collected through a standard chest tube connected to the line 12 in place of the wand 8, as in the case of chest drainage from a traumatic hemothorax or from the mediastinum in post cardiac surgical patients. Anticoagulant may be added as required by means of a connection with the chest tube, the tube 12 or the reservoir 13.

An alternate arrangement is shown in FIG. 2. A bag 19a, generally corresponding to the bag 19, is disposed in a position inverted from that of the bag 19 as shown in the lower portion of FIG. 1. The bag 19a is suspended from the lower hook 22 and alternatively from the upper hook 25 by engagement therewith of the body of a valve 27a corresponding to the valve 27. A flexible conduit 18a, corresponding to the conduit 18, enters into the bag 19a at the end thereof opposite the valve 27a. Another flexible conduit 28a, corresponding to the conduit 28, also enters into the bag 19a at the end opposite the valve 27a.

The operation of the FIG. 2 version of the invention is approximately as described in connection with the FIG. 1 version, a principal exception being that the bag 19a is lifted from the lower hook 22 and without inversion is hung from the higher hook 25. Since the valve 27a is always at the top of the bag 19a, it can readily be used to vent air from the bag 19a or generally to purge this portion of the system.

I claim:

1. An autotransfusion system for a patient who is located at a predetermined elevation comprising a reservoir at a fixed elevation, approximately at said predetermined elevation, a flexible expansible and contractible blood bag, means for supporting said blood bag in one position at a relatively low elevation below said fixed elevation, means for supporting said blood bag in an alternative position at a relatively high elevation above said predetermined elevation, means for conducting fluid from the location of said patient to said reservoir, first flexible means continually connected to said blood bag for delivering said conducted blood from said reservoir to said blood bag at said relatively low elevation, second flexible means continually connected to said blood bag for discharging blood from said blood bag at said relatively high elevation substantially to said patient and valving means in said first and second flexible means for preventing backflow of blood.

2. An autotransfusion system as in claim 1 and including a source of an anticoagulant, and means for connecting said source of anticoagulant to said means for conducting fluid.

3. An autotransfusion system as in claim 1 including means for releasing air from said bag.

4. An autotransfusion system as in claim 1 including a source of anticoagulant and means conducting anticoagulant from said source to said conducting means for blood.

5. An autotransfusion system for a patient who is located at a predetermined elevation comprising a reservoir at a fixed elevation approximately at said predetermined elevation, a single blood bag, means for supporting said blood bag at a low elevation below said fixed elevation, means for supporting said blood bag at a high elevation above said predetermined elevation, means for subjecting the interior of said reservoir to a vacuum, means for conducting fluid including blood substantially from said predetermined elevation to said reservoir, a first tube connected to said reservoir and to said blood bag for delivering said blood by gravity from said reservoir to said blood bag at said low elevation, means including a second tube connected to said blood bag for discharging blood by gravity from said blood bag at said high elevation substantially to said predetermined elevation and valving means in said first and second tubes for preventing backflow of blood.

6. An autotransfusion system for a patient who is located at a predetermined elevation comprising a substantially closed blood reservoir at a fixed elevation approximately at said predetermined elevation, a single blood bag, means for supporting said blood bag at a low elevation below said fixed elevation, means for supporting said blood bag at a high elevation above said predetermined elevation, means for subjecting said blood reservoir to a vacuum, a wand for aspirating atmospheric air and fluid from a location at said predetermined elevation, a first flexible conduit connecting said wand and said reservoir, a needle for injecting blood into said patient, a second flexible conduit continually connecting said reservoir and said blood bag, a third flexible conduit continually connecting said blood bag and said needle and valving means in said second and third flexible conduits for preventing backblow of blood.

7. An autotransfusion system for a patient who is located at a predetermined elevation comprising a blood reservoir at a fixed elevation approximately at said predetermined elevation, a flexible expansible and contractible blood bag, means for supporting said blood bag at a low elevation below said fixed elevation, means for supporting said blood bag at a high elevation above said predetermined elevation, means for subjecting the interior of said blood reservoir to a vacuum, a wand adapted to aspirate fluid from an intermediate elevation, means for connecting said wand and the interior of said reservoir, a flexible tube continually connecting said reservoir and said blood bag, a valve in said flexible tube permitting flow from said reservoir to said blood bag and precluding flow from said blood bag in any elevation thereof to said reservoir, a needle for injecting blood, another flexible tube continually connecting said needle and said blood bag, and another valve in said other flexible tube permitting flow from said blood bag to said needle and precluding flow from said needle to said blood bag at any elevation thereof.

8. An autotransfusion system for a patient who is located at a predetermined elevation comprising a blood reservoir at a fixed elevation approximately at said predetermined elevation, a deformable blood bag, means for supporting said blood bag at a low elevation below said fixed elevation, means for supporting said blood bag at a high elevation above said predetermined elevation, means for subjecting the interior of said reservoir to a vacuum, means for collecting atmospheric air and blood from said patient substantially at said predetermined elevation, a first conduit having a flexible portion for connecting said collecting means to the interior of said reservoir, a source of an anticoagulant, means for conducting said anticoagulant from said source to said collecting means, a needle for injecting blood into said patient, a second flexible conduit for connecting said needle and said blood bag, a check valve in said second conduit for precluding blood flow from said needle to said blood bag, a third flexible conduit connecting said reservoir to said blood bag, and a check valve in said third conduit for precluding flow from said blood bag to said reservoir.

9. An autotransfusion system as in claim 8 in which said source of anticoagulant is vertically adjustable.

10. An autotransfusion system for a patient who is located at a predetermined elevation comprising a blood reservoir at a fixed elevation approximately at said predetermined elevation, a flexible generally closed blood bag, means for supporting said blood bag at a low elevation below said fixed elevation, means for supporting said blood bag at a high elevation above said predetermined elevation, means for subjecting the interior of said reservoir to a vacuum, a wand adapted to aspirate fluid from the vicinity of said predetermined elevation, means including a first flexible conduit for connecting said wand to the interior of said reservoir, a source of an anticoagulant, means for conducting said anticoagulant from said source to said wand and to said first conduit, a needle for injecting blood, a second flexible conduit for connecting said needle and said blood bag, a check valve in said second conduit for precluding blood flow from said needle to said blood bag, a third flexible conduit connecting said reservoir to said blood bag, and another check valve in said third conduit for precluding flow from said blood bag to said reservoir.

11. An autotransfusion system as in claim 10 including a check valve in each of said anticoagulant conducting means, one check valve opening toward said wand from said source of anticoagulant and the other check valve opening toward said first conduit from said source of anticoagulant.

12. An autotransfusion system as in claim 10 in which said means for conducting said anticoagulant to said wand and to said first conduit are first and second tubes, including a check valve in said first tube precluding anticoagulant flow from said wand to said source of anticoagulant, and another check valve in said second tube precluding anticoagulant flow from said first conduit to said source of anticoagulant.

13. An autotransfusion device for a patient who is located at a predetermined elevation, comprising a reservoir at a fixed elevation approximately at said predetermined elevation, means for subjecting said reservoir to a vacuum, an induction element, a flexible conduit connecting said induction element to the interior of said reservoir, a variable volume bag, a first flexible tube connecting the interior of said reservoir and the interior of said bag, valve means in said first flexible tube for preventing flow therein from the interior of said bag to the interior of said reservoir, a discharge element, another flexible tube connecting the interior of said bag and said discharge element, valve means in said other flexible tube for preventing flow therein from said discharge element to the interior of said bag, and means for supporting said bag at an elevation below said reservoir and at another elevation above said discharge element.

* * * * *